United States Patent
Dieckmann et al.

(10) Patent No.: US 9,149,034 B2
(45) Date of Patent: Oct. 6, 2015

(54) AGROCHEMICAL FORMULATIONS COMPRISING CO-POLYMERS BASED ON DIISOCYANATES

(75) Inventors: Yvonne Dieckmann, Hassloch (DE); Michael Ishaque, Mannheim (DE); Ingo Münster, Böhl-Iggelheim (DE); Laurent Picard, Bad Bergzabern (DE); Wolfgang Kerl, Mannheim (DE); Jürgen Langewald, Mannheim (DE); Klaus Kreuz, Denzlingen (DE); Harald Köhle, Bobenheim (DE); Felix Christian Görth, Sewickley, PA (US)

(73) Assignee: BASF SE, Ludwigshafen (DE)

( * ) Notice: Subject to any disclaimer, the term of this patent is extended or adjusted under 35 U.S.C. 154(b) by 609 days.

(21) Appl. No.: 12/515,569

(22) PCT Filed: Nov. 23, 2007

(86) PCT No.: PCT/EP2007/062753
§ 371 (c)(1),
(2), (4) Date: May 20, 2009

(87) PCT Pub. No.: WO2008/065050
PCT Pub. Date: Jun. 5, 2008

(65) Prior Publication Data
US 2010/0029480 A1 Feb. 4, 2010

(30) Foreign Application Priority Data
Nov. 30, 2006 (EP) .................... 06125070

(51) Int. Cl.
| | |
|---|---|
| A01N 47/28 | (2006.01) |
| A01C 1/06 | (2006.01) |
| A01N 37/18 | (2006.01) |
| A01N 25/10 | (2006.01) |

(52) U.S. Cl.
CPC ...................... *A01N 25/10* (2013.01)

(58) Field of Classification Search
None
See application file for complete search history.

(56) References Cited

U.S. PATENT DOCUMENTS

| | | | |
|---|---|---|---|
| 4,822,779 A | 4/1989 | Hwang et al. | |
| 5,169,951 A | 12/1992 | Sutter et al. | |
| 6,221,890 B1 | 4/2001 | Hatakoshi | |
| 6,335,357 B1 | 1/2002 | Okui et al. | |
| 2003/0060471 A1 | 3/2003 | Okui et al. | |
| 2004/0151750 A1* | 8/2004 | O'Leary et al. ............ | 424/405 |
| 2006/0167091 A1 | 7/2006 | Ishii et al. | |
| 2006/0211815 A1 | 9/2006 | Licht et al. | |
| 2008/0207448 A1* | 8/2008 | Marx et al. ............ | 504/100 |
| 2009/0041819 A1* | 2/2009 | Tagami et al. ............ | 424/408 |

(Continued)

FOREIGN PATENT DOCUMENTS

| | | |
|---|---|---|
| EP | 0 454 621 | 10/1991 |
| EP | 0 462 456 | 12/1991 |

(Continued)

OTHER PUBLICATIONS

EPA fact sheet—Boscalid (http://www.epa.gov/pesticides/chem_search/reg_actions/registration/fs_PC-128008_01-Jul-03.pdf) accessed Aug. 9, 2014, dated 2003.*
National Pesticide Center information sheet—Fipronil (http://npic.orst.edu/factsheets/fipronil.pdf) accessed Aug. 9, 2014,available on web Aug. 5, 2003.*
International Search Report completed Jan. 3, 2008, in International Application No. PCT/EP2007/062753, filed Nov. 23, 2007.
International Preliminary Report on Patentability dated Jun. 3, 2009, from corresponding International Application No. PCT/EP2007/062753, filed Nov. 23, 2007.
Database CA [Online] Chemical Abstracts Service, Columbus, Ohio, Us; Takagi, Taiji et al: "Antibacterial waterproofing polyurethane films and their moisture-permeable laminated fabrics" XP002461445 retrieved from STN Database accession No. 2005:135750 Abstract.
Donovan, Stephen F. "Physical Property Requirements of Agrochemicals", Synthesis and Chemistry of Agrochemicals VII, Chapter 2, 2007, pp. 7-22, ACS Symposium Series, vol. 948.

*Primary Examiner* — Mina Haghighatian
*Assistant Examiner* — Erin Hirt
(74) *Attorney, Agent, or Firm* — Brinks Gilson & Lione

(57) ABSTRACT

The present invention comprises formulations comprising at least one pesticide and at least one block copolymer of formula (I) wherein $R^a$ is branched or linear $C_6$-$C_{24}$ alkyl, $C_3$-$C_8$ cycloalkyl, $C_3$-$C_8$ cycloalkyl substituted with $C_1$-$C_6$ alkyl, phenyl, phenyl substituted with $C_1$-$C_6$ alkyl, benzyl, benzyl substituted with $C_1$-$C_6$ alkyl, $C_4$-$C_6$ alkyl substituted with $C_4$-$C_{12}$ alkoxy or $C_1$-$C_4$ alkyl substituted with di ($C_1$-$C_4$ alkyl) amino; $R^b$ is derived from a diisocyanate and $R^c$ is a compound of formula II $(R^1)_n$—X—$(CHR^2CH_2O)_w$—$(CHR^3CH_2O)_x$—$(CHR^4(CH_2)_yO)_z$— (II), in which $R^1$ is hydrogen, or branched or linear, saturated or unsaturated $C_{1\text{-}40}$ alkyl; $R_2$, $R_3$, $R_4$ independently of one another are hydrogen or $C_{1\text{-}4}$ alkyl; w, x, z independently of one another correspond to a value of from 0 to 300; y corresponds to a value of from 1 to 20; X is N or O, where n=1 if X=O, or n=2 if X=N; and the total of w, x and z amounts to at least 1; methods of combating harmful insects and/or phytopathogenic fungi, a method of controlling undesired vegetation and methods of improving the health of plants based on the aforementioned formulations.

(I)

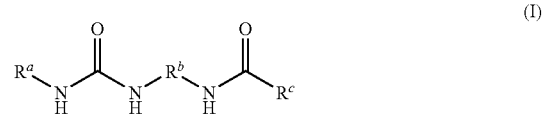

20 Claims, No Drawings

(56) References Cited

U.S. PATENT DOCUMENTS

| | | |
|---|---|---|
| 2010/0048655 A1 | 2/2010 | Koltzenburg et al. |
| 2010/0120617 A1 | 5/2010 | Dyllick-Brenzinger et al. |
| 2010/0122379 A1 | 5/2010 | Dieckmann et al. |
| 2010/0204045 A1* | 8/2010 | Dieckmann et al. .......... 504/100 |

FOREIGN PATENT DOCUMENTS

| | | |
|---|---|---|
| EP | 0 875 557 | 11/1996 |
| JP | 2002193709 | 7/2002 |
| JP | 2002284608 | 10/2002 |
| JP | 2004099597 | 4/2004 |
| JP | 2005042062 | 2/2005 |
| WO | WO 98/28277 | 7/1998 |
| WO | WO 98/28279 | 7/1998 |
| WO | WO 98/45274 | 10/1998 |
| WO | WO 01/00614 | 1/2001 |
| WO | WO 01/70671 | 9/2001 |
| WO | WO 02/48137 | 6/2002 |
| WO | WO 02/089579 | 11/2002 |
| WO | WO 02/090320 | 11/2002 |
| WO | WO 02/090321 | 11/2002 |
| WO | WO 03/007717 | 1/2003 |
| WO | WO 03/007718 | 1/2003 |
| WO | WO 03/015518 | 2/2003 |
| WO | WO 03/024222 | 3/2003 |
| WO | WO 2004/006677 | 1/2004 |
| WO | WO 2004/020399 | 3/2004 |
| WO | WO 2004/033468 | 4/2004 |
| WO | WO 2004/067528 | 8/2004 |
| WO | WO 2004/080180 | 9/2004 |
| WO | WO 2004/101638 | 11/2004 |
| WO | WO 2005/118552 | 12/2005 |
| WO | WO2006/103827 * | 10/2006 ............ A01N 25/12 |
| WO | WO 2008/040786 | 4/2008 |
| WO | WO 2008/064986 | 6/2008 |
| WO | WO 2008/064987 | 6/2008 |
| WO | WO 2008/064990 | 6/2008 |
| WO | WO 2008/132067 | 11/2008 |
| WO | WO 2008/132179 | 11/2008 |

\* cited by examiner

AGROCHEMICAL FORMULATIONS COMPRISING CO-POLYMERS BASED ON DIISOCYANATES

This application is a National Stage application of International Application No. PCT/EP2007/062753 filed Nov. 23, 2007, the entire contents of which is hereby incorporated herein by reference. This application also claims the benefit under 35 U.S.C. §119 of European Patent Application No. 06125070.0 filed Nov. 30, 2006, the entire contents of which is hereby incorporated herein by reference.

The present invention comprises formulations comprising at least one pesticide and at least one block copolymer of formula I $$R^a\underset{H}{N}\overset{O}{\underset{}{\diagup\!\!\!\diagdown}}\underset{H}{N}\!-\!R^b\!-\!\underset{H}{N}\overset{O}{\underset{}{\diagup\!\!\!\diagdown}}R^c \quad (I)$$

wherein
$R^a$ is branched or linear $C_6$-$C_{24}$ alkyl, $C_3$-$C_8$ cycloalkyl, $C_3$-$C_8$ cycloalkyl substituted with $C_1$-$C_6$ alkyl, phenyl, phenyl substituted with $C_1$-$C_6$ alkyl, benzyl, benzyl substituted with $C_1$-$C_6$ alkyl, $C_4$-$C_6$ alkyl substituted with $C_4$-$C_{12}$ alkoxy or $C_1$-$C_4$ alkyl substituted with di($C_1$-$C_4$ alkyl) amino;
$R^b$ is derived from a diisocyanate and
$R^c$ is a compound of formula II $$(R^1)_n\!-\!X\!-\!(CHR^2CH_2O)_w\!-\!(CHR^3CH_2O)_x\!-\!(CHR^4(CH_2)_yO)_z\!- \quad (II),$$

in which
$R^1$ is hydrogen, or branched or linear, saturated or unsaturated $C_{1\text{-}40}$-alkyl;
$R^2$, $R^3$, $R^4$ independently of one another are hydrogen or $C_{1\text{-}4}$-alkyl;
w, x, z independently of one another correspond to a value of from 0 to 300;
y corresponds to a value of from 1 to 20;
X is N or O,
where n=1 if X=O, or n=2 if X=N; and the total of w, x and z amounts to at least 1; methods of combating harmful insects and/or phytopathogenic fungi, a method of controlling undesired vegetation and methods of improving the health of plants based on the afore-mentioned formulations.

Systemic pesticides provide the farmer lots of benefits: The uptake of pesticide of plants, which can be achieved either by seed treatment, foliar treatment or soil treatment, which is the simultaneous or sequential application of seeds and respective formulation (e.g. granule formulations), leads to plants, which are much longer resistant towards pests than plants treated with non-systemic pesticides.

Also for pesticides which provide plant health effects it is desirable to increase their uptake in the plant. The term "plant health" describes for example, advantageous properties such as improved crop characteristics including, but not limited to better emergence, increased crop yields, more favourable protein and/or content, more favourable aminoacid and/or oil composition, more developed root system (improved root growth), tillering increase, increase in plant height, bigger leaf blade, less dead basal leaves, stronger tillers, greener leaf colour, pigment content, photosynthetic activity, less fertilizers needed, less seeds needed, more productive tillers, earlier flowering, early grain maturity, less plant verse (lodging), increased shoot growth, enhanced plant vigor, increased plant stand or early germination; or a combination of at least two or more of the aforementioned effects or any other advantages familiar to a person skilled in the art.

Many pesticides, however, do not show satisfactory systemicity. Furthermore, the systemicity of already systemic pesticides leaves room for improvement.

It is therefore an object of the present invention to improve the systemicity of pesticides, preferably of pesticides with low or no systemicity.

Numerous polymers that are simply useful as solubilizers are known in the art. However, whether any of these polymers is suitable for the above-mentioned purpose is not disclosed in prior art.

The present invention therefore provides formulations comprising at least one pesticide and at least one block copolymer of formula I $$R^a\underset{H}{N}\overset{O}{\underset{}{\diagup\!\!\!\diagdown}}\underset{H}{N}\!-\!R^b\!-\!\underset{H}{N}\overset{O}{\underset{}{\diagup\!\!\!\diagdown}}R^c \quad (I)$$

wherein
$R^a$ is branched or linear $C_6$-$C_{24}$ alkyl, $C_3$-$C_8$ cycloalkyl, $C_3$-$C_8$ cycloalkyl substituted with $C_1$-$C_6$ alkyl, phenyl, phenyl substituted with $C_1$-$C_6$ alkyl, benzyl, benzyl substituted with $C_1$-$C_6$ alkyl, $C_4$-$C_6$ alkyl substituted with $C_4$-$C_{12}$ alkoxy or $C_1$-$C_4$ alkyl substituted with di ($C_1$-$C_4$ alkyl) amino;
$R^b$ is derived from a diisocyanate and
$R^c$ is a compound of formula II $$(R^1)_n\!-\!X\!-\!(CHR^2CH_2O)_w\!-\!(CHR^3CH_2O)_x\!-\!(CHR^4(CH_2)_yO)_z\!- \quad (II),$$

in which
$R^1$ is hydrogen, or branched or linear, saturated or unsaturated $C_{1\text{-}40}$-alkyl;
$R^2$, $R^3$, $R^4$ independently of one another are hydrogen or $C_{1\text{-}4}$-alkyl;
w, x, z independently of one another correspond to a value of from 0 to 300;
y corresponds to a value of from 1 to 20;
X is N or O,
where n=1 if X=O, or n=2 if X=N; and the total of w, x and z amounts to at least 1.

The term "at least one co-polymer" means that one or more co-polymers as defined above can be present in the above-mentioned formulation, i.e. also mixtures of the above-defined co-polymers. Preferably, 1, 2 or 3, more preferably 1 or 2 most preferably 1 copolymer present in the above-mentioned formulation.

The diisocyante from which $R^b$ is derived, is either a cycloalphatic or aliphatic (hereinafter referred to as (cyclo) aliphatic) or aromatic diisocyanate.

Examples of diisocyanates are monomeric methylene di(phenylisocyanate) (MDI), toluene diisocyanate (TDI), naphthyl diisocyanate (NDI), hexamethylene diisocyanate (HDI), isophorone diisocyanate (IPDI), 2,4 and 2,6-diisocyanatomethylcyclohexane ($H_6$TDI) and the isomer mixtures thereof, o-, m- or p-xylene diisocyanate (XDI), diisocyanatocyclohexane (t-CHDI), di(isocyanatocyclohexyl)methane ($H_{12}$MDI), tetramethyl-m-xylylene diisocyanate (m-TMXDI), 1,3-bis(isocyanatomethyl)cyclohexane ($H_6$XDI), diisocyanatocyclohexane (t-CHDI), 4,4-diphenylmethane diisocyanate, diisocyanatobutane, 1,6-diisocyanato-2,2,4,4-tetramethylhexane, 1,6-diisocyanato-2,2,4-trimethylhexane and mixtures thereof (TMDI).

Preferred diisocyanates are asymmetric diisocyanates that posses isocyanate groups with different reactivities. Herein, TDI and IPDI are preferred. Most preferred diisocyanate is IPDI.

Particular embodiments of the compound of the formula (II)

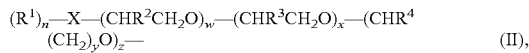

result
a) in the event that w, x and z are zero (non-alkoxylated alcohol residues);
b) in the event that z corresponds to a value of from 1 to 300 and w and x are zero (alkoxylates such as ethoxylates ($R^4$=H; y=1) or propoxylates ($R^4$=$CH_3$; y=1);
c) in the event that w is zero and x and z independently of one another correspond to a value of from 1 to 300 (EO-PO block copolymers with, for example, an EO-PO block arrangement (y=1; $R^3$=$CH_3$; $R^4$=H) or a PO-EO block arrangement (y=1; $R^3$=H; $R^4$=$CH_3$);
d) in the event that w, x and z independently of one another correspond to a value of from 1 to 300 (EO-PO-EO block copolymers with, for example, an EO-PO-EO block arrangement (y=1; $R^2$=H; $R^3$=$CH_3$; $R^4$=H) or a PO-EO-PO block arrangement (y=1; $R^2$=$CH_3$; $R^3$=H; $R^4$=$CH_3$)).

The above-mentioned polymers of formula II may be statistic polymers, block co-polymers or random co-polymers.

Alcohol residues which have proved suitable in accordance with the invention are, in particular, optionally alkoxylated residues of the formula (II) in which $R^1$ is an alkyl radical having preferably 1 to 30 carbon atoms. In one preferred embodiment, $R^1$ is a longer-chain radical, which has preferably 8 to 24 carbon atoms being preferred. In another embodiment, $R^1$ is methyl.

Very especially suitable alcohol alkoxylates and especially alcohol ethoxylate residues are those of the formula (IIa)

in which
$R^1$ has the above meaning and is, preferably, branched or linear, saturated or unsaturated $C_8$-$C_{24}$-alkyl or methyl; and
z corresponds to a value of from 1 to 100 and is preferably between 1 and 20.

The term "$C_1$-$C_4$-alkyl" as used herein refers to a branched or unbranched saturated hydrocarbon group having 1 to 4 carbon atoms, for example methyl, ethyl, propyl, 1-methylethyl, butyl, 1-methylpropyl and 2-methylpropyl.

The term "$C_1$-$C_6$-alkyl" as used herein refers to a branched or unbranched saturated hydrocarbon group having 1 to 6 carbon atoms, for example the compounds listed for $C_1$-$C_4$ alkyl 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl.

The term "$C_4$-$C_{12}$ alkoxy" as used herein refers to a branched or unbranched saturated $C_4$-$C_{12}$ alkyl group having from 4 to 12 carbon atoms which is bonded via an oxygen, for example for example, butoxy, 1-methylpropoxy, 2-methylpropoxy or 1,1-dimethylethoxy, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy, hexoxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methoxypropoxy, 1-ethyl-2-methoxypropyl, heptoxy, octoxy, 2-ethylhexoxy, n-nonoxy, iso-nonoxy, n-decoxy, iso-decoxy, n-undecoxy, iso-undecoxy, n-dodecoxy, iso-dodecoxy and their isomers.

The term "$C_9$-$C_{24}$-alkyl" as used herein refers to a branched or unbranched saturated hydrocarbon group having 9 to 24 carbon atoms, for example 2-ethylhexyl, n-nonyl, iso-nonyl, n-decyl, iso-decyl, n-undecyl, iso-undecyl, n-dodecyl, iso-dodecyl, n-tridecyl, iso-tridecyl, stearyl and n-eicosyl and their isomers.

The term "$C_6$-$C_{24}$-alkyl" as used herein refers to a branched or unbranched saturated hydrocarbon group having 6 to 24 carbon atoms, for example hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, n-nonyl, iso-nonyl, n-decyl, iso-decyl, n-undecyl, iso-undecyl, n-dodecyl, iso-dodecyl, n-tridecyl, iso-tridecyl, stearyl and n-eicosyl and their isomers.

The term "$C_1$-$C_{40}$-alkyl" as used herein refers to a branched or unbranched saturated hydrocarbon group having 1 to 40 carbon atoms including those examples listed for $C_1$-$C_4$ alkyl and $C_8$-$C_{24}$ alkyl.

The term "$C_3$-$C_8$-cycloalkyl" as used herein refers to a monocyclic 3- to 8-membered saturated carbon atom ring, e.g. cyclopropyl, cyclobutyl, cyclopentyl, cyclohexyl, cycloheptyl and cyclooctyl;

The term "$C_1$-$C_6$ substituted phenyl" as used herein refers to a phenyl group, which may carry one, two or more $C_1$-$C_6$ alkyl-substituents. Preferably, this term refers to a phenyl group, which carries one or two $C_1$-$C_6$ alkyl substituents.

Preferably, $R^a$ is branched or linear $C_6$-$C_{24}$ alkyl, $C_3$-$C_8$ cycloalkyl, phenyl, $C_1$-$C_3$ substituted phenyl, benzyl, $C_4$-$C_6$ alkyl substituted with $C_4$-$C_{12}$ alkoxy or —$C_1$-$C_4$ alkyl substituted with di ($C_1$-$C_4$ alkyl) amino, more preferably phenyl, 2,6-dimethylphenyl, dodecyl, ethylhexyl), cyclohexyl, benzyl, ethylhexyl, di(methyl)propylamino or 3-(2-ethylhexoxy) propyl, most preferably 2,6-dimethylphenyl, dodecyl, cyclohexyl or benzyl.

The term "$C_1$-$C_3$ substituted phenyl" as used herein refers to a phenyl group, which may carry one, two or more $C_1$-$C_3$ alkyl-substituents such as ethyl, methly, propyl or i-propyl. Preferably, this term refers to a phenyl group, which carries one or two $C_1$-$C_4$ alkyl substituents.

The preparation of polymers according to the invention can be performed according to methods known in the art, for example by reacting a diisocyanate as exemplified above with an alcohol of formula IIa

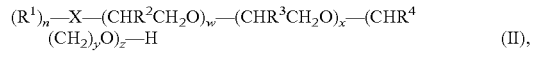

wherein the substituents have the meaning given above, preferably in a molar ratio of 1:1. For reactions with a symmetric diisocyanate it can be suitable to work with am excess of diisocyanate. After completion of the reaction, an amin of formula II

$NH_2R^a$ (III)

wherein $R^a$ has the meaning given above, is added.

Alkohols of formula II can be prepared according to methods known in the art. They are also for example commerical available (for example Lutensol® and Pluriol® trademarks from BASF).

The reaction is carried out preferably in organic solvents such as ketones, e.g. acetone or methylethyl ketone, furthermore dimethylsulfoxide, dimethylformamide, or in general aprotic-polar organic solvents or mixtures of such solvents.

Preferably the reaction is carried out in the presence of a catalyst. Suitable catalysts are e.g. organometallic compounds such as organotitanium compounds or tin compounds, e.g. dibutyl tin dilaurate or tin octoate, furthermore bases such as 1,4-diaza(2,2,2)bicyclooctane or tetramethylbutanediamine. The catalyst is present in amounts of 0.05 to 0.2 mol per mole diisocyanate.

When the NCO number indicates that the reaction was quantitative an amine $NH_2-R^a$ is added to the reaction mixture forming an urea group with the remaining isocyanate group.

The reaction is carried out at temperatures between 150 and 25° C., preferably between 40 and 100° C.

All embodiments of the above-mentioned polymers are referred herein below as "polymers according to the present invention".

The present invention also comprises the use of polymers according to the present invention for increasing the systemicity of pesticides. This is achieved contacting the pesticide with a certain amount of polymer according to the present invention e.g. in an agrochemical formulation as set forth above.

In general, the formulations comprise from 0.1 to 99% by weight of the polymer according to the present invention, preferably from 1 to 85% by weight, more preferably from 3 to 70% by weight, most preferably from 5 to 60% by weight.

In general, the formulations comprise from 0.1 to 90% by weight, preferably from 1 to 85% by weight, of the pesticide(s), more preferably from 3 to 80% by weight, most preferably from 3 to 70% by weight.

The weight by weight ratio of polymer:pesticide is preferably 20:1-1:20 (w/w), more preferably 10:1-1:10 (w/w), most preferably 3:1-1:3 (w/w).

The term "at least one pesticide" within the meaning of the invention states that one or more compounds can be selected from the group consisting of fungicides, insecticides, nematicides, herbicide and/or safener or growth regulator, preferably from the group consisting of fungicides, insecticides or nematicides, most preferably from the group consisting of fungicides. Also mixtures of pesticides of two or more the aforementioned classes can be used. The skilled artisan is familiar with such pesticides, which can be, for example, found in the Pesticide Manual, 13th Ed. (2003), The British Crop Protection Council, London.

The following list of pesticides is intended to illustrate the possible combinations, but not to impose any limitation:

The insecticide/nematicide is selected from the group consisting of

The following list of pesticides together with which the compounds according to the invention can be used, is intended to illustrate the possible combinations, but not to impose any limitation:

A.1. Organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;

A.2. Carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;

A.3. Pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin;

A.4. Growth regulators: a) chitin synthesis inhibitors: benzoylureas: chlorfluazuron, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramat;

A.5. Nicotinic receptor agonists/antagonists compounds: clothianidin, dinotefuran, imidacloprid, thiamethoxam, nitenpyram, acetamiprid, thiacloprid; the thiazol compound of formula ($\Delta^1$)

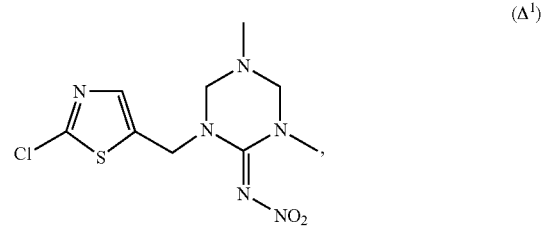 [SMILES: CN1CN(C)/C(=N\[N+](=O)[O-])N(Cc2cnc(Cl)s2)C1]

A.6. GABA antagonist compounds: acetoprole, endosulfan, ethiprole, fipronil, vaniliprole, pyrafluprole, pyriprole, the phenylpyrazole compound of formula $\Delta^2$

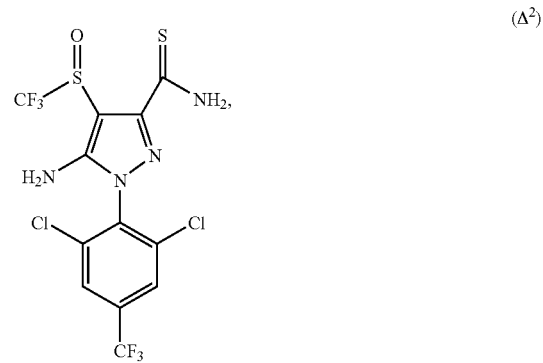

A.7. Macrocyclic lactone insecticides: abamectin, emamectin, milbemectin, lepimectin, spinosad, the compound of formula ($\Delta^3$) (CAS No. 187166-40-1)

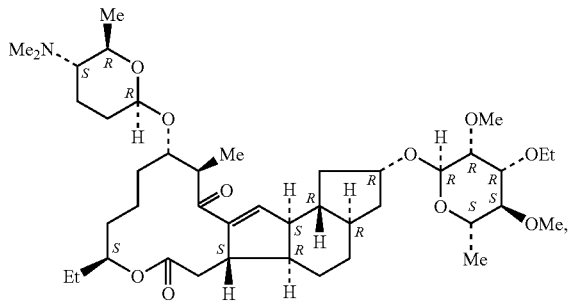

A.8. METI I compounds: fenazaquin, pyridaben, tebufenpyrad, tolfenpyrad, flufenerim;
A.9. METI II and III compounds: acequinocyl, fluacyprim, hydramethylnon;
A.10. Uncoupler compounds: chlorfenapyr;
A.11. Oxidative phosphorylation inhibitor compounds: cyhexatin, diafenthiuron, fenbutatin oxide, propargite;
A.12. Moulting disruptor compounds: cyromazine;
A.13. Mixed Function Oxidase inhibitor compounds: piperonyl butoxide;
A.14. Sodium channel blocker compounds: indoxacarb, metaflumizone,
A.15. Various: benclothiaz, bifenazate, cartap, flonicamid, pyridalyl, pymetrozine, sulfur, thiocyclam, flubendiamide, cyenopyrafen, flupyrazofos, cyflumetofen, amidoflumet, the aminoquinazolinone compound of formula $\Delta^4$

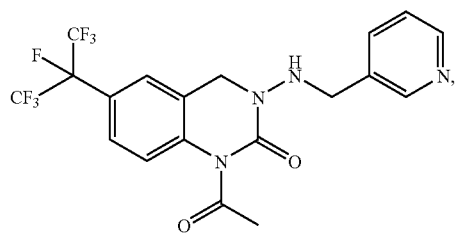

N—R'-2,2-dihalo-1-R"cyclo-propanecarboxamide-2-(2,6-dichloro-α,α,α-tri-fluoro-p-tolyl)hydrazone or N—R'-2,2-di(R''')propionamide-2-(2,6-dichloro-α,α,α-trifluoro-p-tolyl)-hydrazone, wherein R' is methyl or ethyl, halo is chloro or bromo, R" is hydrogen or methyl and R''' is methyl or ethyl, anthranilamide compounds of formula $\Delta^5$

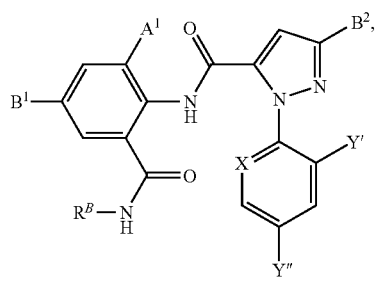

wherein $A^1$ is $CH_3$, Cl, Br, I, X is C—H, C—Cl, C—F or N, Y' is F, Cl, or Br, Y" is F, Cl, $CF_3$, $B^1$ is hydrogen, Cl, Br, I, CN, $B^2$ is Cl, Br, $CF_3$, $OCH_2CF_3$, $OCF_2H$, and $R^B$ is hydrogen, $CH_3$ or $CH(CH_3)_2$, and malononitrile compounds as described in JP 2002 284608, WO 02/89579, WO 02/90320, WO 02/90321, WO 04/06677, WO 04/20399, or JP 2004 99597.

The commercially available compounds of the group A may be found in The Pesticide Manual, 13th Edition, British Crop Protection Council (2003) among other publications. Thiamides of formula $\Delta^2$ and their preparation have been described in WO 98/28279. Lepimection is known from Agro Project, PJB Publications Ltd, November 2004. Benclothiaz and its preparation have been described in EP-A1 454621. Methidathion and Paraoxon and their preparation have been described Farm Chemicals Handbook, Volume 88, Meister Publishing Company, 2001. Acetoprole and its preparation have been described in WO 98/28277. Metaflumizone and its preparation have been described in EP-A1 462 456. Flupyrazofos has been described in Pesticide Science 54, 1988, p. 237-243 and in U.S. Pat. No. 4,822,779. Pyrafluprole and its preparation have been described in JP 2002193709 and in WO 01/00614. Pyriprole and its preparation have been described in WO 98/45274 and in U.S. Pat. No. 6,335,357. Amidoflumet and its preparation have been described in U.S. Pat. No. 6,221,890 and in JP 21010907. Flufenerim and its preparation have been described in WO 03/007717 and in WO 03/007718. Cyflumetofen and its preparation have been described in WO 04/080180.

Anthranilamides of formula $\Delta^5$ and their preparation have been described in WO 01/70671; WO 02/48137; WO 03/24222, WO 03/15518, WO 04/67528; WO 04/33468; and WO 05/118552.

The fungicide can be selected from the group consisting of
1. Strobilurins such as azoxystrobin, dimoxystrobin, enestroburin, fluoxastrobin, kresoxim-methyl, metominostrobin, picoxystrobin, pyraclostrobin, trifloxystrobin, orysastrobin, methyl (2-chloro-5-[1-(3-methylbenzyloxyimino)ethyl]benzyl)carbamate, methyl (2-chloro-5-[1-(6-methylpyridin-2-ylmethoxyimino)ethyl]benzyl)carbamate, methyl 2-(ortho-((2,5-dimethylphenyloxymethylene)phenyl)-3-methoxyacrylate;
2. Carboxamides such as
    carboxanilides: benalaxyl, benodanil, boscalid, carboxin, mepronil, fenfuram, fenhexamid, flutolanil, furametpyr, metalaxyl, ofurace, oxadixyl, oxycarboxin, penthiopyrad, thifluzamide, tiadinil, N-(4'-bromobiphenyl-2-yl)-4-difluoromethyl-2-methylthiazole-5-carboxamide, N-(4'-trifluoromethylbiphenyl-2-yl)-4-difluoromethyl-2-methylthiazole-5-carboxamide, N-(4'-chloro-3'-fluorobiphenyl-2-yl)-4-difluoromethyl-2-methylthiazole-5-carboxamide, N-(3',4'-dichloro-4-fluorobiphenyl-2-yl)-3-difluoromethyl-1-methylpyrazole-4-carboxamide, N-(2-cyanophenyl)-3,4-dichloroisothiazole-5-carboxamide;
    carboxylic acid morpholides: dimethomorph, flumorph;
    benzamides: flumetover, fluopicolide (picobenzamid), zoxamide;
    other carboxamides: carpropamid, diclocymet, mandipropamid, N-(2-(4-[3-(4-chlorophenyl) prop-2-ynyloxy]-3-methoxyphenyl)ethyl)-2-methanesulfonylamino-3-methylbutyramide, N-(2-(4-[3-(4-chlorophenyl)prop-2-ynyloxy]-3-methoxyphenyl)ethyl)-2-ethanesulfonylamino-3-methylbutyramide, N-(3',4'-dichloro-5-fluorobiphenyl-2-yl)-3-difluoromethyl-1-methylpyrazole-4-carboxamide and 3-Difluoromethyl-1-methyl-1H-pyrazole-4-carboxylic acid (2-bicyclopropyl-2-yl-phenyl)-amide;
3. Azoles such as
    triazoles: bitertanol, bromuconazole, cyproconazole, difenoconazole, diniconazole, enilconazole, epoxiconazole, fenbuconazole, flusilazole, fluquinconazole, flutriafol, hexaconazole, imibenconazole, ipconazole, metconazole, myclobutanil, penconazole, propiconazole, prothioconazole, simeconazole, tebuconazole, tetraconazole, triadimenol, triadimefon, triticonazole;

imidazoles: cyazofamid, imazalil, pefurazoate, prochloraz, triflumizole;

benzimidazoles: benomyl, carbendazim, fuberidazole, thiabendazole;

others: ethaboxam, etridiazole, hymexazole;

4. Nitrogenous heterocyclyl compounds such as
pyridines: fluazinam, pyrifenox, 3-[5-(4-chlorophenyl)-2,3-dimethylisoxazolid in-3-yl]-pyridine;
pyrimidines: bupirimate, cyprodinil, ferimzone, fenarimol, mepanipyrim, nuarimol, pyrimethanil;
piperazines: triforine;
pyrroles: fludioxonil, fenpiclonil;
morpholines: aldimorph, dodemorph, fenpropimorph, tridemorph;
dicarboximides: iprodione, procymidone, vinclozolin;
others: acibenzolar-5-methyl, anilazine, captan, captafol, dazomet, diclomezine, fenoxanil, folpet, fenpropidin, famoxadone, fenamidone, octhilinone, probenazole, proquinazid, pyroquilon, quinoxyfen, tricyclazole, 5-chloro-7-(4-methylpiperidin-1-yl)-6-(2,4,6-trifluorophenyl)-[1,2,4]triazolo[1,5-a]pyrimidine, 2-butoxy-6-iodo-3-propylchromen-4-one, N,N-dimethyl-3-(3-bromo-6-fluoro-2-methylindole-1-sulfonyl)-[1,2,4]triazole-1-sulfonamide;

5. Carbamates and dithiocarbamates such as
dithiocarbamates: ferbam, mancozeb, maneb, metiram, metam, propineb, thiram, zineb, ziram;
carbamates: diethofencarb, flubenthiavalicarb, iprovalicarb, propamocarb, methyl 3-(4-chlorophenyl)-3-(2-isopropoxycarbonylamino-3-methylbutyrylamino)propionate, 4-fluorophenyl N-(1-(1-(4-cyanophenyl)ethanesulfonyl)but-2-yl)carbamate 6. Other fungicides such as
guanidines: dodine, iminoctadine, guazatine;
antibiotics: kasugamycin, polyoxins, streptomycin, validamycin A;
organometallic compounds: fentin salts;
sulfur-containing heterocyclyl compounds: isoprothiolane, dithianon;
organophosphorus compounds: edifenphos, fosetyl, fosetyl-aluminum, iprobenfos, pyrazophos, tolclofos-methyl, phosphorous acid and its salts;
organochlorine compounds: thiophanate-methyl, chlorothalonil, dichlofluanid, tolylfluanid, flusulfamide, phthalide, hexachlorbenzene, pencycuron, quintozene;
nitrophenyl derivatives: binapacryl, dinocap, dinobutoni;
inorganic active compounds: Bordeaux mixture, copper acetate, copper hydroxide, copper oxychloride, basic copper sulfate, sulfur;
others: spiroxamine, cyflufenamid, cymoxanil, metrafenone.

The herbicide is selected from the group consisting of
b1) lipid biosynthesis inhibitors such as chlorazifop, clodinafop, clofop, cyhalofop, diclofop, fenoxaprop, fenoxaprop-p, fenthiaprop, fluazifop, fluazifop-P, haloxyfop, haloxyfop-P, isoxapyrifop, metamifop, propaquizafop, quizalofop, quizalofop-P, trifop, alloxydim, butroxydim, clethodim, cloproxydim, cycloxydim, profoxydim, sethoxydim, tepraloxydim, tralkoxydim, butylate, cycloate, diallate, dimepiperate, EPTC, esprocarb, ethiolate, isopolinate, methiobencarb, molinate, orbencarb, pebulate, prosulfocarb, sulfallate, thiobencarb, tiocarbazil, triallate, vernolate, benfuresate, ethofumesate and bensulide;

b2) ALS inhibitors such as amidosulfuron, azimsulfuron, bensulfuron, chlorimuron, chlorsulfuron, cinosulfuron, cyclosulfamuron, ethametsulfuron, ethoxysulfuron, flazasulfuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, imazamethabenz, imazamox, imazapic, imazapyr, imazaquin, imazethapyr, cloransulam, diclosulam, florasulam, flumetsulam, metosulam, penoxsulam, bispyribac, pyriminobac, propoxycarbazone, flucarbazone, pyribenzoxim, pyriftalid and pyrithiobac;

b3) photosynthesis inhibitors such as atraton, atrazine, ametryne, aziprotryne, cyanazine, cyanatryn, chlorazine, cyprazine, desmetryne, dimethametryne, dipropetryn, eglinazine, ipazine, mesoprazine, methometon, methoprotryne, procyazine, proglinazine, prometon, prometryne, propazine, sebuthylazine, secbumeton, simazine, simeton, simetryne, terbumeton, terbuthylazine, terbutryne, trietazine, ametridione, amibuzin, hexazinone, isomethiozin, metamitron, metribuzin, bromacil, isocil, lenacil, terbacil, brompyrazon, chloridazon, dimidazon, desmedipham, phenisopham, phenmedipham, phenmedipham-ethyl, benzthiazuron, buthiuron, ethidimuron, isouron, methabenzthiazuron, monoisouron, tebuthiuron, thiazafluoron, anisuron, buturon, chlorbromuron, chloreturon, chlorotoluron, chloroxuron, difenoxuron, dimefuron, diuron, fenuron, fluometuron, fluothiuron, isoproturon, linuron, methiuron, metobenzuron, metobromuron, metoxuron, monolinuron, monuron, neburon, parafluoron, phenobenzuron, siduron, tetrafluoron, thidiazuron, cyperquat, diethamquat, difenzoquat, diquat, morfamquat, paraquat, bromobonil, bromoxynil, chloroxynil, iodobonil, ioxynil, amicarbazone, bromofenoxim, flumezin, methazole, bentazone, propanil, pentanochlor, pyridate, and pyridafol;

b4) protoporphyrinogen-IX oxidase inhibitors such as acifluorfen, bifenox, chlomethoxyfen, chlornitrofen, ethoxyfen, fluorodifen, fluoroglycofen, fluoronitrofen, fomesafen, furyloxyfen, halosafen, lactofen, nitrofen, nitrofluorfen, oxyfluorfen, fluazolate, pyraflufen, cinidon-ethyl, flumiclorac, flumioxazin, flumipropyn, fluthiacet, thidiazimin, oxadiazon, oxadiargyl, azafenidin, carfentrazone, sulfentrazone, pentoxazone, benzfendizone, butafenacil, pyraclonil, profluazol, flufenpyr, flupropacil, nipyraclofen and etnipromid;

b5) bleacher herbicides such as metflurazon, norflurazon, flufenican, diflufenicani, picolinafen, beflubutamid, fluridone, fluorochloridone, flurtamone, mesotrione, sulcotrione, isoxachlortole, isoxaflutole, benzofenap, pyrazolynate, pyrazoxyfen, benzobicyclon, amitrole, clomazone, aclonifen, 4-(3-trifluoromethylphenoxy)-2-(4-trifluoromethylphenyl) pyrimidine, and also 3-heterocyclyl-substituted benzoyl derivatives of the formula II (see in WO 96/26202, WO 97/41116, WO 97/41117 and WO 97/41118)

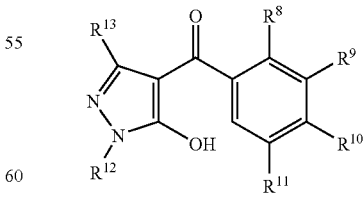

in which the variables $R^8$ to $R^{13}$ are as defined below:
$R^8$, $R^{10}$ are hydrogen, halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl or $C_1$-$C_6$-alkylsulfonyl;
$R^9$ is a heterocyclic radical selected from the group consisting of such as thiazol-2-yl, thiazol-4-yl, thiazol-5-yl, isoxazol-3- yl, isoxazol-4-yl, isoxazol-5-yl, 4,5-dihydroisoxazol-3-yl, 4,5-dihydroisoxazol-4-yl and 4,5-dihydroisoxazol-5-yl, where the nine radicals mentioned may be unsubstituted or mono- or polysubstituted, e.g. mono-, di-, tri- or tetrasubstituted, by halogen, $C_1$-$C_4$-alkyl, $C_1$-$C_4$-alkoxy, $C_1$-$C_4$-haloalkyl, $C_1$-$C_4$-haloalkoxy or $C_1$-$C_4$-alkylthio;

$R^{11}$ is hydrogen, halogen or $C_1$-$C_6$-alkyl;

$R^{12}$ is $C_1$-$C_6$-alkyl;

$R^{13}$ is hydrogen or $C_1$-$C_6$-alkyl.

b6) EPSP synthase inhibitors such as glyphosate;

b7) glutamine synthase inhibitors such as glufosinate and bilanaphos;

b8) DHP synthase inhibitors such as asulam;

b9) mitose inhibitors such as benfluralin, butralin, dinitramine, ethalfluralin, fluchloralin, isopropalin, methalpropalin, nitralin, oryzalin, pendimethalin, prodiamine, profluralin, trifluralin, amiprofos-methyl, butamifos, dithiopyr, thiazopyr, propyzamide, tebutam, chlorthal, carbetamide, chlorbufam, chlorpropham and propham;

b10) VLCFA inhibitors such as acetochlor, alachlor, butachlor, butenachlor, delachlor, diethatyl, dimethachlor, dimethenamid, dimethenamid-P, metazachlor, metolachlor, S-metolachlor, pretilachlor, propachlor, propisochlor, prynachlor, terbuchlor, thenylchlor, xylachlor, allidochlor, CDEA, epronaz, diphenamid, napropamide, naproanilide, pethoxamid, flufenacet, mefenacet, fentrazamide, anilofos, piperophos, cafenstrole, indanofan and tridiphane;

b11) cellulose biosynthesis inhibitors such as dichlobenil, chlorthiamid, isoxaben and flupoxam;

b12) decoupler herbicides such as dinofenate, dinoprop, dinosam, dinoseb, dinoterb, DNOC, etinofen and medinoterb;

b13) auxin herbicides such as clomeprop, 2,4-D, 2,4,5-T, MCPA, MCPA thioethyl, dichlorprop, dichlorprop-P, mecoprop, mecoprop-P, 2,4-DB, MCPB, chloramben, dicamba, 2,3,6-TBA, tricamba, quinclorac, quinmerac, clopyralid, fluoroxypyr, picloram, triclopyr and benazolin;

b14) auxin transport inhibitors such as naptalam, diflufenzopyr;

b15) benzoylprop, flamprop, flamprop-M, bromobutide, chlorflurenol, cinmethylin, methyldymron, etobenzanid, fosamine, metam, pyributicarb, oxaziclomefone, dazomet, triaziflam and methyl bromide.

Suitable safeners can be selected from the following listing: benoxacor, cloquintocet, cyometrinil, dichlormid, dicyclonon, dietholate, fenchlorazole, fenclorim, flurazole, fluxofenim, furilazole, isoxadifen, mefenpyr, mephenate, naphthalic anhydride, 2,2,5-trimethyl-3-(dichloroacetyl)-1,3-oxazolidine (R-29148), 4-(dichloroacetyl)-1-oxa-4-azaspiro[4.5]decane (AD-67; MON 4660) and oxabetrinil Generally, fungicides and insecticides are preferred.

Preferred insecticides are azinphos-methyl, chlorpyrifos, chlorpyrifos-methyl, chlorfenvinphos, diazinon, disulfoton, ethion, fenitrothion, fenthion, isoxathion, malathion, methidathion, methyl-parathion, parathion, phenthoate, phosalone, phosmet, phorate, phoxim, pirimiphos-methyl, profenofos, prothiofos, sulprophos, tetrachlorvinphos, terbufos, alanycarb, benfuracarb, carbosulfan, fenoxycarb, furathiocarb, methiocarb, triazamate; chlorfluazuron, diflubenzuron, flucycloxuron, flufenoxuron, hexaflumuron, lufenuron, novaluron, teflubenzuron, triflumuron; methoxyfenozide, tebufenozide, azadirachtin pyriproxyfen, methoprene, fenoxycarb; spirodiclofen, spiromesifen, spirotetramat; clothianidin, dinotefuran, imidacloprid, thiamethoxam, nitenpyram, acetamiprid, thiacloprid; acetoprole, endosulfan, ethiprole, fipronil, vaniliprole, pyrafluprole, pyriprole, the phenylpyrazole compound of formula $\Delta^2$

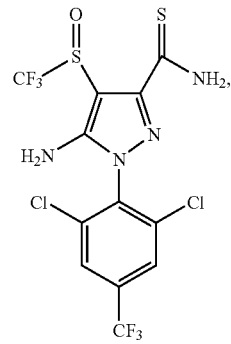

(A²)

abamectin, emamectin, milbemectin, lepimectin, fenazaquin, pyridaben, tebufenpyrad, acequinocyl, fluacyprim, hydramethylnon, chlorfenapyr, cyhexatin, diafenthiuron, fenbutatin oxide, propargite, piperonyl butoxide; indoxacarb, metaflumizone, bifenazate, pymetrozine, N—R'-2,2-dihalo-1-R"cyclo-propanecarboxamide-2-(2,6-dichloro-α,α,α-tri-fluoro-p-tolyl)hydrazone or N—R'-2,2-di(R''')propionamide-2-(2,6-dichloro-α,α,α-trifluoro-p-tolyl)-hydrazone, wherein R' is methyl or ethyl, halo is chloro or bromo, R" is hydrogen or methyl and R''' is methyl or ethyl More preferred insecticides are cyfluthrin, λ-cyhalothrin, cypermethrin, alpha-cypermethrin, beta-cypermethrin, deltamethrin, esfenvalerate, fenvalerate, permethrin, tefluthrin, tetramethrin, transfluthrin, flufenoxuron, teflubenzuron, clothianidin, thiamethoxam, acetamiprid, ethiprole, fipronil, phenylpyrazole compound of formula $\Delta^2$

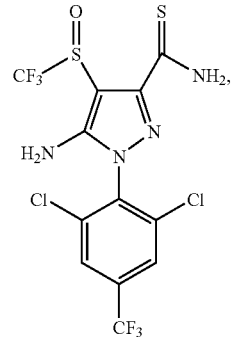

(A²)

chlorfenapyr; piperonyl butoxide; indoxacarb, metaflumizone, pymetrozine, N—R'-2,2-dihalo-1-R"cyclo-propanecarboxamide-2-(2,6-dichloro-α,α,α-tri-fluoro-p-tolyl)hydrazone or N—R'-2,2-di(R''')propionamide-2-(2,6-dichloro-α,α,α-trifluoro-p-tolyl)hydrazone, wherein R' is methyl or ethyl, halo is chloro or bromo, R" is hydrogen or methyl and R''' is methyl or ethyl.

Preferred fungicides are azoxystrobin, dimoxystrobin, fluoxastrobin, kresoxim-methyl, picoxystrobin, pyraclostrobin, trifloxystrobin, orysastrobin, methyl 2-(ortho-((2,5-dimethylphenyloxymethylene)phenyl)-3-methoxyacrylate; boscalid, metalaxyl, penthiopyrad, N-(3',4'-dichloro-4-fluorobiphenyl-2-yl)-3-difluoromethyl-1-methylpyrazole-4-carboxamide, dimethomorph, fluopicolide (picobenzamid), zoxamide; mandipropamid, N-(3',4'-dichloro-5-fluorobiphenyl-2-yl)-3-difluoromethyl-1-methylpyrazole-4-carboxamide, 3-Difluoromethyl-1-methyl-1H-pyrazole-4-carboxylic acid (2-bicyclopropyl-2-yl-phenyl)-amide, cyproconazole, difenoconazole, epoxiconazole, fluquinconazole, metconazole, propiconazole, prothioconazole, tebuconazole, triticonazole; cyazofamid, prochloraz, ethaboxam, fluazinam, cyprodinil, pyrimethanil; triforine; fludioxonil, dodemorph, fenpropimorph, tridemorph, vinclozolin, dazomet, fenoxanil, fenpropidin, proquinazid; flubenthiavalicarb, iprovalicarb, dodine, dithianon, fosetyl, fosetyl-aluminum, chlorothalonil, spiroxamine, cyflufenamid, cymoxanil, metrafenone.

More preferred fungicides are azoxystrobin, dimoxystrobin, fluoxastrobin, kresoxim-methyl, picoxystrobin, pyraclostrobin, trifloxystrobin, orysastrobin, boscalid, metalaxyl, N-(3',4'-dichloro-4-fluorobiphenyl-2-yl)-3-difluoromethyl-1-methylpyrazole-4-carboxamide, dimethomorph, fluopicolide (picobenzamid), zoxamide; mandipropamid: N-(3',4'-dichloro-5-fluorobiphenyl-2-yl)-3-difluoromethyl-1-methylpyrazole-4-carboxamide, 3-Difluoromethyl-1-methyl-1H-pyrazole-4-carboxylic acid (2-bicyclopropyl-2-yl-phenyl)-amide, cyproconazole, difenoconazole, epoxiconazole, metconazole, propiconazole, prothioconazole, tebuconazole, cyazofamid, prochloraz, cyprodinil, triforine; fludioxonil, dodemorph, fenpropimorph, tridemorph, vinclozolin, dazomet, fenoxanil, iprovalicarb, dodine, dithianon, fosetyl, fosetyl-aluminum, chlorothalonil, spiroxamine, metrafenone.

Most preferred fungicides are azoxystrobin, fluoxastrobin, picoxystrobin, pyraclostrobin, trifloxystrobin, orysastrobin, boscalid, metalaxyl, N-(3',4'-dichloro-4-fluorobiphenyl-2-yl)-3-difluoromethyl-1-methylpyrazole-4-carboxamide, dimethomorph, fluopicolide (picobenzamid), zoxamide; mandipropamid, 3-Difluoromethyl-1-methyl-1H-pyrazole-4-carboxylic acid (2-bicyclopropyl-2-yl-phenyl)-amide-cyproconazole, difenoconazole, epoxiconazole, propiconazole, prothioconazole, tebuconazole, prochloraz, cyprodinil, fludioxonil, iprovalicarb, fosetyl, fosetyl-aluminum, chlorothalonil, spiroxamine, metrafenone.

As mentioned above, in one embodiment of the invention, also pesticides can be used, which confer plant health effects. Such pesticides are known in the art. Suitable for this purpose are, for example an active compound that inhibits the mitochondrial breathing chain at the level of the b/c1 complex;

carboxylic amides selected from benalaxyl, benodanil, boscalid, carboxin, mepronil, fenfuram, fenhexamid, flutolanil, furametpyr, metalaxyl, ofurace, oxadixyl, oxycarboxin, penthiopyrad, thifluzamid, tiadinil, 4-difluoromethyl-2-methyl-thiazol-5-carboxylic acid-(4'-bromo-biphenyl-2-yl)-amide, 4-difluoromethyl-2-methyl-thiazol-5-carboxylic acid-(4'-trifluoromethyl-biphenyl-2-yl)-amide, 4-difluoromethyl-2-methyl-thiazol-5-carboxylic acid-(4'-chloro-3'-fluoro-biphenyl-2-yl)-amide, 3-difluoromethyl-1-methyl-pyrazol-4-carboxylic acid-(3',4'-dichloro-4-fluoro-biphenyl-2-yl)-amide, 3,4-dichloro-isothiazol-5-carboxylic acid-(2-cyano-phenyl)-amide, dimethomorph, flumorph, flumetover, fluopicolide (picobenzamid), zoxamide, carpropamide, diclocymet, mandipropamid, N-(2-(4-[3-(4-chloro-phenyl)-prop-2-inyloxy]-3-methoxy-phenyl)-ethyl)-2-methanesulfonylamino-3-methyl-butyramid and N-(2-(4-[3-(4-chloro-phenyl)-prop-2-inyloxy]-3-methoxy-phenyl)-ethyl)-2-ethanesulfonylamino-3-methyl-butyramide;

azoles selected from bitertanol, bromuconazole, cyproconazole, difenoconazole, diniconazole, enilconazole, epoxiconazole, fenbuconazole, flusilazole, fluquinconazole, flutriafol, hexaconazole, imibenconazole, ipconazole, metconazole, myclobutanil, penconazole, propiconazole, prothioconazole, simeconazole, tebuconazole, tetraconazole, triadimenol, triadimefon, triticonazole, cyazofamid, imazalil, pefurazoate, prochloraz, triflumizol, benomyl, carbendazim, fuberidazole, thiabendazole, ethaboxam, etridiazole and hymexazole;

nitrogen-containing heterocyclic compounds selected from fluazinam, pyrifenox, 3-[5-(4-chloro-phenyl)-2,3-dimethyl-isoxazolidin-3-yl]-pyridine, bupirimat, cyprodinil, ferimzon, fenarimol, mepanipyrim, nuarimol, pyrimethanil, triforin, fludioxonil, fenpiclonil, aldimorph, dodemorph, fenpropimorph, tridemorph, iprodion, procymidon, vinclozolin, acibenzolar-5-methyl, anilazin, captan, captafol, dazomet, diclomezine, fenoxanil, folpet, fenpropidin, famoxadone, fenamidone, octhilinon, probenazol, proquinazid, pyroquilon, quinoxyfen, tricyclazol, 2-butoxy-6-iodo-3-propyl-chromen-4-one, 3-(3-bromo-6-fluoro-2-methyl-indole-1-sulfonyl)-[1,2,4]triazole-1-sulfonic acid dimethylamide;

carbamates and dithiocarbamates selected from ferbam, mancozeb, metiram, metam, propineb, thiram, zineb, ziram, diethofencarb, flubenthiavalicarb, iprovalicarb, propamocarb, 3-(4-chloro-phenyl)-3-(2-isopropoxycarbonylamino-3-methyl-butyrylamino)-propionic acid methylester and N-(1-(1-(4-cyanophenyl)ethanesulfonyl)-but-2-yl) carbamic acid-(4-fluorophenyl)ester;

guanidines selected from dodin, iminoctadine and guazatin;

antibiotics selected from kasugamycin, polyoxine, streptomycin and validamycin A;

fentin salts;

sulfur-containing heterocyclic compounds selected from isoprothiolan and dithianon;

organophosphorous compounds selected from edifenphos, fosetyl, fosetyl-aluminium, iprobenfos, pyrazophos, tolclofos-methyl, phosphoric acid and the salts thereof;

organo-chloro compounds selected from thiophanate methyl, chlorothalonil, dichlofluanid, tolylfluanid, flusulfamid, phthalide, hexachlorbenzene, pencycuron, quintozen;

nitrophenyl derivatives selected from binapacryl, dinocap and dinobuton;

inorganic active ingredients selected from Bordeaux composition, copper acetate, copper hydroxide, copper oxychloride, basic copper sulfate and sulfur;

spiroxamine; cyflufenamide; cymoxanil; metrafenone;

organo(thio)phosphates selected from acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methylparathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos and trichlorfon;

carbamates selected from alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicar and triazamate;

pyrethroids selected from allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin and profluthrin, dimefluthrin;

growth regulators selected from a) chitin synthesis inhibitors that are selected from the benzoylureas chlorfluazuron, diflubenzuron, flucycloxuron, flufenoxuron, hexaflumuron, lufenuron, novaluron, teflubenzuron, triflumuron; buprofezin, diofenolan, hexythiazox, etoxazole and clofentazine; b) ecdysone antagonists that are selected from halofenozide, methoxyfenozide, tebufenozide and azadirachtin; c) juvenoids that are selected from pyriproxyfen, methoprene and fenoxycarb and d) lipid biosynthesis inhibitors that are selected from spirodiclofen, spiromesifen and spirotetramat;

nicotinic receptor agonists/antagonists compounds selected from clothianidin, dinotefuran, (EZ)-1-(6-chloro-3-pyridyl-methyl)-N-nitroimidazolidin-2-ylideneamine (imidacloprid), (EZ)-3-(2-chloro-1,3-thiazol-5-ylmethyl)-5-methyl-1,3,5-oxadiazinan-4-ylidene(nitro)amine (thiamethoxam), nitenpyram, acetamiprid, thiacloprid;
the thiazol compound of formula (Γ¹)

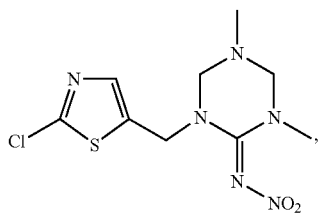

(Γ¹)

GABA antagonist compounds selected from acetoprole, endosulfan, ethiprole, 5-amino-1-(2,6-dichloro-α,α,α-trifluoro-p-tolyl)-4-trifluoromethylsulfinylpyrazole-3-carbonitrile (fipronil), vaniliprole, pyrafluprole, pyriprole and the phenylpyrazole compound of formula Γ²

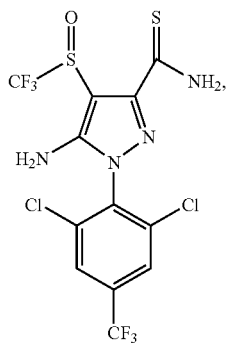

(Γ²)

METI I compounds selected from fenazaquin, pyridaben, tebufenpyrad, tolfenpyrad and flufenerim;
METI II and III compounds selected from acequinocyl, fluacyprim and hydramethylnon;
chlorfenapyr;
oxidative phosphorylation inhibitor compounds selected from cyhexatin, diafenthiuron, fenbutatin oxide and propargite;
cyromazine; piperonyl butoxide; indoxacarb; benclothiaz; bifenazate, cartap, flonicamid, pyridalyl, pymetrozine, sulfur, thiocyclam, flubendiamide, cyenopyrafen, flupyrazofos, cyflumetofen, amidoflumet, the aminoquinazolinone compound of formula Γ⁴

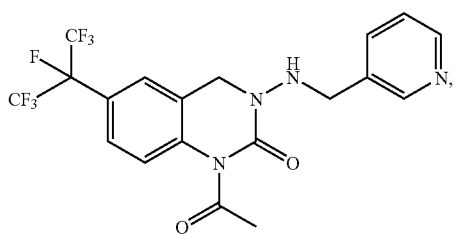

(Γ⁴)

and anthranilamide compounds of formula Γ⁵

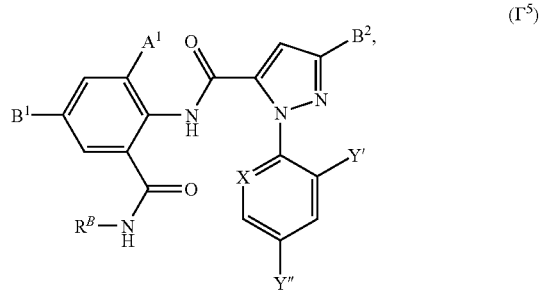

(Γ⁵)

wherein $A^1$ is $CH_3$, Cl, Br, I, X is C—H, C—Cl, C—F or N, Y' is F, Cl, or Br, Y" is F, Cl, $CF_3$, $B^1$ is hydrogen, Cl, Br, I, CN, $B^2$ is Cl, Br, $CF_3$, $OCH_2CF_3$, $OCF_2H$, and $R^B$ is hydrogen, $CH_3$ or $CH(CH_3)_2$.

wherein pyraclostrobin, azoxystrobin, kresoximmethyl, trifloxystrobin, picoxystrobin, dimoxystrobin, fluoxastrobin, orysastrobin, tebuconazole, difenoconazole, epoxiconazole, cyproconazole, prothioconazol, propiconazole, fipronil, imidacloprid and thiamethoxam are preferred.

As set forth above, the polymers according to the present invention can be used for the preparation of formulations comprising at least one pesticide and the polymer according to the present invention. Optionally, formulations comprising at least one pesticide and at least one polymer according to the present invention may comprise further formulation auxiliaries.

In general, the formulations comprise from 0 to 90% by weight, preferably from 1 to 85% by weight, more preferably from 5 to 80% by weight, most preferably from 5 to 65% by weight of the formulation auxiliaries.

The term "formulation auxiliaries" within the meaning of the invention is auxiliaries suitable for the formulation of pesticides, such as further solvents and/or carriers and/or surfactants (ionic or non-ionic surfactants, adjuvants, dispersing agents) and/or preservatives and/or antifoaming agents and/or anti-freezing agents and optionally, for seed treatment formulations colorants and/or binders and/or gelling agents and/or thickeners.

Examples of suitable solvents are water, aromatic solvents (for example Solvesso products, xylene), paraffins (for example mineral oil fractions such as kerosene or diesel oil), coal tar oils and oils of vegetable or animal origin, aliphatic, cyclic and aromatic hydrocarbons, for example toluene, xylene, paraffin, tetrahydronaphthalene, alkylated naphthalenes or their derivatives, alcohols (for example methanol, butanol, pentanol, benzyl alcohol, cyclohexanol), ketones (for example cyclohexanone, gamma-butyrolactone), pyrrolidones (NMP, NEP, NOP), acetates (glycol diacetate), glycols, fatty acid dimethylamides, fatty acids and fatty acid esters, isophorone and dimethylsulfoxide. In principle, solvent mixtures may also be used.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenol ethers, ethoxylated isooctylphenol, octylphenol, nonylphenol, alkylphenol polyglycol ethers, tributylphenyl polyglycol ethers, tristearylphenyl polyglycol ethers, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Examples of suitable carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders, polyvinylpyrrolidone and other solid carriers.)

Also anti-freezing agents such as glycerin, ethylene glycol, hexylene glycol, propylene glycol and bactericides such as can be added to the formulation.

Suitable antifoaming agents are for example antifoaming agents based on silicon or magnesium stearate.

Suitable preservatives are for example 1,2-benzisothiazolin-3-one and/or 2-Methyl-2H-isothiazol-3-one or sodium benzoate or benzoic acid.

Examples of thickeners (i.e., compounds which bestow a pseudoplastic flow behavior on the formulation, i.e. high viscosity at rest and low viscosity in the agitated state) are, for example, polysaccharides or organic or inorganic layered minerals, such as xanthan gum (Kelzan® from Kelco), Rhodopol® 23 (Rhône-Poulenc) or Veegum® (R.T. Vanderbilt) or Attaclay® (Engelhardt).

Seed Treatment formulations may additionally comprise binders and optionally colorants.

Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Binders can be added to improve the adhesion of the active materials on the seeds after treatment. Suitable binders are: polyvinylpyrrolidone, polyvinylacetate, polyvinylalkohol and tylose.

The use forms of the formulations (for example in the form of directly sprayable solutions, powders, suspensions or dispersions, emulsions, oil dispersions, pastes, dustable products, materials for spreading, or granules) depend entirely on the intended purposes; they are intended to ensure in each case the finest possible distribution of the pesticide and polymer according to the invention.

Examples of suitable formulation types in which the polymer according to the present invention can be used are
1. Liquid Formulations such as
EC (Emulsifiable concentrate) formulation; SL or LS (Soluble concentrate) formulation; EW (Emulsion, oil in water) formulation ME (Microemulsion) formulation MEC Microemulsifiable concentrates concentrate formulation CS (Capsule suspension) formulation TK (Technical concentrate) formulation, OD (oil based suspension concentrate) formulation; SC (suspension concentrate) formulation; SE (Suspo-emulsion) formulation; ULV (Ultra-low volume liquid) formulation; SO (Spreading oil) formulation; AL (Any other liquid) formulation; LA (Lacquer) formulation; DC (Dispersible concentrate) formulation;
2. Solid Formulations such as
WG (Water dispersible granules) formulation; TB (Tablet) formulation; FG (Fine granule) formulation; MG (Microgranule) formulation; SG (soluble Granule)

Preferred are formulation types such as EC (Emulsifiable concentrate) formulation; SL or LS (Soluble concentrate) formulation; EW (Emulsion, oil in water) formulation ME (Microemulsion) formulation, CS (Capsule suspension) formulation, OD (oil based suspension concentrate) formulation; SC (suspension concentrate) formulation; SE (Suspoemulsion) formulation; DC (Dispersible concentrate) formulation, WG (Water dispersible granules) formulation; TB (Tablet) formulation); FG (Fine granule) formulation and SG (soluble Granule).

The invention also includes a process for the preparation of a formulation according to the present invention. The processes used in this connection are generally familiar to a person skilled in the art and are, for example, described in the literature cited with the various formulation types (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. No. 4,172,714, U.S. Pat. No. 4,144,050, U.S. Pat. No. 3,920,442, U.S. Pat. No. 5,180,587, U.S. Pat. No. 5,232,701, U.S. Pat. No. 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8).

Liquid formulations can be prepared by mixing or combining the polymer according to the invention with at least one pesticide and or further formulation auxiliaries.

Powders, materials for spreading and dustable products can be prepared by mixing or concomitantly grinding the active substances with a solid carrier.

Granules, for example coated granules, impregnated granules and homogeneous granules, can be prepared by binding the active compounds to solid carriers.

The above-referred formulations can be used as such or use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; it is intended to ensure in each case the finest possible distribution of the pesticid(es) and polymer according to the invention.

Aqueous use forms can be prepared also from emulsion concentrates, pastes or wettable powders (sprayable powders, oil dispersions) by adding a suitable solvent, for example water.

In general, the polymer according to the present invention can be added to an already prepared formulation or included in a formulation comprising at least one pesticide and at least one polymer according to the present invention. The addition of the polymer to the formulation can be performed prior or after dilution of the formulation in water; e.g. preparing a formulation as mentioned before containing the polymer according to this invention or adding the polymer after dilution of the pesticide formulation in a suitable solvent, for example water (e.g. as so called tank mix)

All embodiments of the above-mentioned application are herein below referred to as "formulation according to the present invention".

The present invention furthermore comprises a method of combating harmful insects and/or phytopathogenic fungi, which comprises contacting plants, seed, soil or habitat of plants in or on which the harmful insects and/or phytopathogenic fungi are growing or may grow, plants, seed or soil to be protected from attack or infestation by said harmful insects and/or phytopathogenic fungi with an effective amount of a agrochemical formulation according to the present invention.

The formulations according to the present invention can therefore be used for the control of a multitude of phytopaghogenic fungi or insects on various cultivated plants or weeds in, such as wheat, rye, barley, oats, rice, corn, grass, bananas, cotton, soy, coffee, sugar cane, vines, fruits and ornamental plants, and vegetables, such as cucumbers, beans, tomatoes, potatoes and cucurbits, and on the seeds of these plants.

The present invention furthermore comprises a method of improving the health of plants, which comprises applying a formulation according to the present invention, wherein the pesticide is a pesticide which confers plant health effects, to plants, parts of plants, or the locus where plants grow.

The present invention furthermore comprises a method of controlling undesired vegetation, which comprises allowing a herbicidally effective amount of a agrochemical formulation according to the present invention to act on plants, their habitat or on seed of said plants.

Thus, the formulations according to the present invention compositions according to the present invention are suitable for controlling common harmful plants in useful plants, in particular in crops such as oat, barley, millet, corn, rice, wheat, sugar cane, cotton, oilseed rape, flax, lentil, sugar beet, tobacco, sunflowers and soybeans or in perennial crops.

The term phytopathogenic fungi includes but is not limited to the following species:
*Alternaria* species on vegetables, rapeseed, sugar beet and fruit and rice (for example *A. solani* or *A. alternata* on potato and other plants); *Aphanomyces* species on sugar beet and vegetables; *Bipolaris* and *Drechslera* species on corn, cereals, rice and lawns (for example *D. teres* on barley, *D. tritci-repentis* on wheat); *Blumeria graminis* (powdery mildew) on cereals; *Botrytis cinerea* (gray mold) on strawberries, vegetables, flowers and grapevines; *Bremia lactucae* on lettuce; *Cercospora* species on corn, soybeans, rice and sugar beet (for example *C. beticula* on sugar beet); *Cochliobolusi* species on corn, cereals, rice (for example *Cochliobolus sativus* on cereals, *Cochliobolus miyabeanus* on rice); *Colletotricum* species on soybeans, cotton and other plants (for example *C. acutatum* on various plants); Esca on grapes caused by *Phaeoacremonium chlamydosporium, Ph. Aleophilum,* and *Formitipora punctata* (syn. *Phellinus punctatus*); *Exserohilum* species on corn; *Erysiphe cichoracearum* and *Sphaerotheca fuliginea* on cucurbits; *Fusarium* and *Verticillium* species (for example *V. dahliae*) on various plants (for example *F. graminearum* on wheat); *Gaeumanomyces graminis* on cereals; *Gibberella* species on cereals and rice (for example *Gibberella fujikuroi* on rice); Grainstaining complex on rice; *Helminthosporium* species (for example *H. graminicola*) on corn and rice; *Michrodochium nivale* on cereals; *Mycosphaerella* species on cereals, bananas and peanuts (*M. graminicola* on wheat, *M. fijiesis* on bananas); *Phakopsara pachyrhizi* and *Phakopsara meibomiae* on soybeans; *Phomopsis* species on soybeans, sunflowers and grapevines (*P. viticola* on grapevines, *P. helianthii* on sunflowers); *Phytophthora infestans* on potatoes and tomatoes; *Plasmopara viticola* on grapevines; *Podosphaera leucotricha* on apples; *Pseudocercosporella herpotrichoides* on cereals; *Pseudoperonospora* species on hops and cucurbits (for example *P. cubenis* on cucumbers); *Puccinia* species on cereals, corn and asparagus (*P. triticina* and *P. striformis* on wheat, *P. asparagi* on asparagus); *Pyrenophora* species on cereals; *Pyricularia oryzae, Corticium sasakii, Sarocladium oryzae, S. attenuatum, Entyloma oryzae* on rice; *Pyricularia* grisea on lawns and cereals; *Pythium* spp. on lawns, rice, corn, cotton, rapeseed, sunflowers, sugar beet, vegetables and other plants; *Rhizoctonia*-species (for example *R. solani*) on cotton, rice, potatoes, lawns, corn, rapeseed, potatoes, sugar beet, vegetables and other plants; *Rhynchosporium secalis* e.g. on rye and barley; *Sclerotinia* species (for example *S. sclerotiorum*) on rapeseed, sunflowers and other plants; *Septoria tritici* and *Stagonospora nodorum* on wheat; *Erysiphe* (syn. *Uncinula necator*) on grapevines; *Setospaeria* species on corn and lawns; *Sphacelotheca reilinia* on corn; *Thievaliopsis* species on soybeans and cotton; *Tilletia* species on cereals; *Ustilago* species on cereals, corn and sugar beet and; *Venturia* species (scab) on apples and pears (for example *V. inaequalis* on apples). They are particularly suitable for controlling harmful fungi from the class of the Oomycetes, such as *Peronospora* species, *Phytophthora* species, *Plasmopara viticola* and *Pseudoperonospora* species.

The formulations according to the present invention can also be used for controlling harmful fungi in the protection of material such as wood. Examples of fungi are Ascomycetes, such as *Ophiostoma* spp., *Ceratocystis* spp., *Aureobasidium pullulans, Sclerophoma* spp., *Chaetomium* spp., *Humicola* spp., *Petriella* spp., *Trichurus* spp.; Basidiomycetes, such as *Coniophora* spp., *Coriolus* spp., *Gloeophyllum* spp., *Lentinus* spp., *Pleurotus* spp., *Poria* spp., *Serpula* spp. and *Tyromyces* spp., Deuteromycetes, such as *Aspergillus* spp., *Cladosporium* spp., *Penicillium* spp., *Trichoderma* spp., *Alternaria* spp., *Paecilomyces* spp. and Zygomycetes, such as *Mucor* spp., The invention furthermore relates to a method for controlling undesirable vegetation in crops, in particular in crops of oat, barley, millet, corn, rice, wheat, sugar cane, cotton, oilseed rape, flax, lentil, sugar beet, tobacco, sunflowers and soybeans or in perennial crops, which comprises allowing a effective amount of a agrochemical formulation according to the present invention to act on plants, their habitat or on seed of said plants.

The invention furthermore relates to a method for controlling undesirable vegetation in crops which, by genetic engineering or by breeding, are resistant to one or more herbicides and/or fungicides and/or or to attack by insects, which comprises allowing a effective amount of a agrochemical formulation according to the present invention to act on plants, their habitat or on seed of said plants.

The control of undesired vegetation is understood as meaning the destruction of weeds. Weeds, in the broadest sense, are understood as meaning all those plants which grow in locations where they are undesired, for example:

Dicotyledonous weeds of the genera: *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Taraxacum.*

Monocotyledonous weeds of the genera: *Echinochloa, Setaria, Panicum, Digitaria, Phleum, Poa, Festuca, Eleusine,*

Brachiaria, Lolium, Bromus, Avena, Cyperus, Sorghum, Agropyron, Cynodon, Monochoria, Fimbristyslis, Sagittaria, Eleocharis, Scirpus, Paspalum, Ischaemum, Sphenoclea, Dactyloctenium, Agrostis, Alopecurus, Apera.

Thus, as set forth above, formulations according to the invention can be applied via various methods.

In one embodiment of the present invention, foliar application of the formulation according to the present invention is carried out, e.g. by spraying or dusting or otherwise applying the mixture to the seeds, the seedlings, the plants.

Another embodiment of the present invention comprises soil treatment, e.g by spraying or dusting or otherwise applying the mixture to the soils before (e.g. by soil drench) or after sowing of the plants or before or after emergence of the plants.

In accordance with one variant of soil application, a further subject of the invention is a method of treating soil by the application, in particular into the seed drill.

In accordance with one variant of soil application, a further subject of the invention is in furrow treatment, which comprises adding a solid or liquid formulation to the open furrow, in which seeds have been sown or, alternatively, applying seeds and formulation simultaneously to the open furrow Another embodiment of the present invention comprises the treatment of seeds or seedlings from plants.

The term seed treatment comprises all suitable seed treatment techniques known in the art, such as seed dressing, seed coating, seed dusting, seed soaking and seed pelleting.

Thus, the application of the formulation according to the present invention is carried out by spraying or dusting or otherwise applying the formulation according to the present invention to the seeds or the seedlings.

The present invention also comprises seeds coated with formulation according to the present invention.

The term seed embraces seeds and plant propagules of all kinds including but not limited to true seeds, seed pieces, suckers, corms, bulbs, fruit, tubers, grains, cuttings, cut shoots and the like and means in a preferred embodiment true seeds.

Suitable seed is seed of cereals, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, Brassica species, melons, beans, peas, garlic, onions, carrots, tuberous plants such as potatoes, sugar cane, tobacco, grapes, petunias, geranium/pelargoniums, pansies and impatiens.

In addition, the formulation according to the invention may also be used for the treatment seeds from plants, which tolerate the action of herbicides or fungicides or insecticides owing to breeding, including genetic engineering methods, for example seeds of transgenic crops which are resistant to herbicides from the group consisting of the sulfonylureas (EP-A-0257993, U.S. Pat. No. 5,013,659), imidazolinones (see for example U.S. Pat. No. 6,222,100, WO0182685, WO0026390, WO9741218, WO9802526, WO9802527, WO 04/106529, WO 05/20673, WO 03/14357, WO 03/13225, WO 03/14356, WO 04/16073), glufosinate-type (see for example EP-A-0242236, EP-A-242246) or glyphosate-type (see for example WO 92/00377) or in seeds of plants resistant towards herbicides selected from the group of cyclohexadienone/Aryloxyphenoxypropionic acid herbicides (U.S. Pat. No. 5,162,602, U.S. Pat. No. 5,290,696, U.S. Pat. No. 5,498, 544, U.S. Pat. No. 5,428,001, U.S. Pat. No. 6,069,298, U.S. Pat. No. 6,268,550, U.S. Pat. No. 6,146,867, U.S. Pat. No. 6,222,099, U.S. Pat. No. 6,414,222) or in seeds of transgenic crop plants, for example cotton, with the capability of producing Bacillus thuringiensis toxins (Bt toxins) which make the plants resistant to certain pests (EP-A-0142924, EP-A-01 93259)

The seed treatment application of the formulation according to the invention is carried out by spraying or dusting the seeds before sowing of the plants and before emergence of the plants by methods known to the skilled artisan.

In the treatment of seeds the corresponding formulations are applied by treating the seeds with an effective amount of the formulation according to the present invention. Herein, the application rates of pesticide are generally from 0.1 g to 10 kg per 100 kg of seed, preferably from 1 g to 5 kg per 100 kg of seed, in particular from 1 g to 2.5 kg per 100 kg of seed. For specific crops such as lettuce or onion, the rate can be higher.

For the purpose of the present invention, seed treatment and soil (or habitat of plant) treatment is preferred.

The invention is further illustrated but not limited by the following examples.

EXAMPLES

To prepare the polymers, the following apparatus was used: 1l apparatus with process controlled water-bath, anchor stirrer and thermometer. The apparatus had connectors for 3 feeds, a reflux condenser and an inlet tube for introducing nitrogen or steam.

The number of free NCO-groups was determined via potentiometric titration with a "SM Titrino 720". For this the 0.5-5 g reaction mixture is diluted in about 70 ml NMP and an excess of n-dibutylamine (~20 ml) is added. The excess n-dibutylamine is than titrated with 0.1N HCl.

Abbreviations used:
NMP N-methylpyrrolidone
IPDI isophorone diisocyanate
DABCO 1,4-diazabicyclo-[2.2.2]-octane
NCO isocyanate
ai active ingredient
Bcq Becquerel
DMF dimethyl formamide
ppm mg/kg
C10-oxoalcool ethoxylate Ethoxylated short chain, synthetic, saturated fatty alcohol with a degree of ethoxylation of about 3, a hydroxy number of 190 mg KOH/g and a molar mass of about 290 g/mol.
methyl polyethylenglycol Methoxypolyethylene glycol with a hydroxy number of 160 mg KOH/g and a molar mass of about 350 g/mol.

Example 1

Preparation of Polymer A

Preparation of a block copolymer consisting of 2,6-xylidine and a C10-oxoalcohol ethoxylate coupled via IPDI.

The initial charge (174 g C10-oxoalcool ethoxylate and 380.5 g methyl ethyl ketone) was gassed with nitrogen and heated to a reactor internal temperature of 50° C. Feed 1 (133.4 g IPDI and 0.36 g DABCO) was then introduced within 5 minutes. An exothermic reaction was observable. When the number of free NCO-groups indicated full conversion feed 2 (72.7 g xylidine) was added within 5 minutes. When the NCO-number indicated full conversion the vessel was cooled down to room temperature.

Example 2

Preparation of Polymers B-G

The preparation of polymers B-G was carried out analogously to example 1. The amounts and substances used for Initial charge, feed 1 and 2 are set forth in table 1.

TABLE 1

|  | Initial Charge | Feed 1 | Feed 2 |
|---|---|---|---|
| Polymer B | 174 g C10-oxoalcohol ethoxylate; 372 g methyl ethyl ketone | 133.4 g IPDI 0.36 g DABCO | 59.4 g dodecylamine |
| Polymer C | 174 g C10-oxoalcohol ethoxylate 367.2 g methyl ethyl ketone | 133.4 g IPDI 0.36 g DABCO | 59.4 g cyclohexylamine |
| Polymer D | 174 g C10-oxoalcohol ethoxylate; 369 g methyl ethyl ketone | 133.4 g IPDI; 0.36 g DABCO | 61.2 g dimethyl-amino propylamine |
| Polymer E | 174 g C10-oxoalcohol ethoxylate 420 g methyl ethyl ketone | 133.4 g IPDI 0.42 g DABCO | 112.2 g 3-(2-ethyl-hexoxy)propylamine |
| Polymer F | 210 g methyl polyethylenglycol 407.9 g methyl ethyl ketone | 133.3 g IPDI 0.4 g DABCO | 64.2 g benzylamine |
| Polymer G | 210 g methyl polyethylenglycol 454.9 g methyl ethyl ketone | 133.3 g IPDI 0.4 g DABCO | 111.2 g dodecyl amine |

Example 3

Root uptake A) Test with radioactively marked ai

To test the root systemicity of the ai, radioactively marked boscalid (prepared in analogy to EP 0545099 based on $^{14}$C marked pyridin) was used. For the tests wheat plants in vermiculite were drenched with boscalid/polymer solutions in water/acetone mixtures. As reference boscalid solutions in water/acetone mixtures without polymers were used [25 µl cold active solution (10000 ppm stock solution in acetone), 20 µl hot active solution (0.1 ppm in acetone, 1 µl corresponds to ~22000 Bcq), 25 µl acetone and 25 µl polymer solution (10000 ppm stock solution in water) were mixed and refilled with water to 10 ml. After 48 and 120 hours leafs were cut from the plant and dissolved in Soluene 350 (60-80% toluene, 20-40% dodecyl(dimethyl)(tetradecyl)ammonium hydroxide, 2.5-10% methanol). Afterwards the radioactivity in the plant material was measured. High radioactivity in the plant material corresponds to high active ingredient uptake. Results are presented in table 2:

TABLE 2

| Polymer | Uptake [Bcq]* |
|---|---|
| Reference without polymer | 219 |
| A | 602 |
| B | 896 |
| C | 533 |
| D | 508 |
| E | 478 |
| F | 583 |

*active ingredient uptake after 120 hours

The results show that with the polymers A to F significant improved root uptake was achieved.

B) Test with Pathogenes

For testing, the following solutions were prepared in a first step:
To test the polymers with the actual pathogenes, tomatoe plants were directly grown in hoagland solution. Hoagland solution consists of the following ingredients 0.25 v % of 1M KNO$_3$ solution in water, 0.1 v % of 1M MgSO$_4$ solution in water, 0.05 v % of 1M KH$_2$PO$_4$ solution in water, 0.25 v % 1M Ca(NO$_3$)$_2$) solution in water, 0.05 v % of a trace solution consisting of 2.86 g/l H$_3$BO$_3$, 1.81 g/l MnCl$_2$*4H$_2$O, 0.22 g/l ZnSO$_4$*7H$_2$O, 0.08 g/l CuSO$_4$*5H$_2$O, 0.016 g/l MoO$_3$ in water, 0.075 v % Sequestrene 138 Fe consisting of 30 g/l sodium ferric ethylenediamine di-(o-hydroxyphenylacetate) in water, 99.225 v % water sterilized and pH adjusted to 6-6.5 with NaOH.

After 16 days the plants were transfered to containers with 240 ml boscalid or boscalid/polymer (the ratio boscalid/polymer is 1:1 per weight) solutions (1.3, 0.43, 0.14 and 0.05 ppm) in Hoagland solution containing 0.8 vol % acetone. 6 days after the ai application the plants were infested with fungus (Alteria, ALTESO P6 (Bayer)). After 5 additional days the infestation was rated (column "Infestation Rating") and plants that had not been treated with ai were used as reference for 100% infestation.

Two separate experiments were performed. In one test, polymers A and B were tested (see table 3), in the other experiment, polymers C and F were tested (see table 4). Results are presented in tables 3 and 4.

TABLE 3

| polymer | Active (or Polymer/Active) concentration [ppm] | Infestation Rating |
|---|---|---|
| untreated | 0 | 100% |
| ai without polymer | 1.3 | 1% |
|  | 0.43 | 13% |
|  | 0.14 | 60% |
|  | 0.05 | 77% |
| A | 1.3 | 0% |
|  | 0.43 | 3% |
|  | 0.14 | 15% |
|  | 0.05 | 67% |
| B | 1.3 | 1% |
|  | 0.43 | 9% |
|  | 0.14 | 23% |
|  | 0.05 | 60% |

TABLE 4

| polymer | Active (or Polymer/Active) concentration [ppm] | Rating |
|---|---|---|
| ai without polymer | 1.3 | 0% |
|  | 0.43 | 17% |
|  | 0.14 | 47% |
|  | 0.05 | 53% |
| C | 1.3 | 0% |
|  | 0.43 | 5% |
|  | 0.14 | 20% |
|  | 0.05 | 43% |

TABLE 4-continued

| polymer | Active (or Polymer/Active) concentration [ppm] | Rating |
|---|---|---|
| F | 1.3 | 0% |
|  | 0.43 | 7% |
|  | 0.14 | 17% |
|  | 0.05 | 37% |

The results show that with the polymers A to F, significant improved pathogen control was achieved.

Example 4

Leaf Uptake

To test the leaf uptake with polymers water/DMF solutions with radioactively marked boscalid (1 μl cold active solution (10000 ppm solution in DMF), 10 μl hot active solution (0.1 ppm in DMF, ~2000000 counts/μl), 9 μl polymer solution (1000 ppm solution in water) and 80 μl DMF) were applied dropwise to the leaves of a wheat plants (10 drops per leap. After 48 and 168 hours respectively. The leaves were cut off after the respective time and the excess active on the leaf surface eliminated by stripping the leaf with a cellulose acetate film. The leaves were then dissolved with Soluene 350 to determine the absolute amount of active ingredient that was taken up into the plant. As reference the active was applied in water/DMF solution without polymer. Results are presented in table 5.

TABLE 5

| Polymer | Uptake [% applied]* |
|---|---|
| Reference without polymer | 1.3 |
| D | 6.3 |
| F | 25.8 |

*uptake determined after 168 hours.

The results show that with the polymers D and F significant improved leaf uptake was achieved.

Example 5

Seed Treatment

To test the polymers, 100 μL COSMOS® 50 FS (a commercially available aqueous suspension concentrate for seed treatment from BASF Aktiengesellschaft comprising 500 g/L fipronil) was mixed with 1100 μL of a 4.5 wt % polymer solution in water. As a reference ("COSMOS®® 50 FS without polymer") a mixture of 100 μL COSMOS® 50 FS in 1100 μL water was used. Then 100 sugar beet seeds were treated twice with 300 μl polymer/COSMOS® 50 FS mixture (corresponding to 25 g Fipronil/100 kg seed and 25 g polymer/100 kg seed), and another 100 seeds w ere treated twice with 300 μl of the reference ("COSMOS® 50 FS without polymer").

The seeds of sugar-beets were sown in soil containing styropor-boxes under greenhouse conditions. Samples were taken at a plant height of about 10-15 cm. After sampling the plants (both treatment groups) were subdivided into two segments (hypocotyl and rest of plant). The samples were frozen immediately after sampling and kept frozen until analysis. Prior to analyses the sample material was homogenized using a Stephansmill in the presence of dry ice resulting in very small sample particles.

Fipronil was extracted from plant matrices using a mixture of methanol and water. For clean-up a liquid/liquid partition against dichloromethane was used. The final determination of fipronil content was performed by HPLC-MS/MS. Results are presented in table 6.

TABLE 6

|  |  | Fipronil concentration [ppm] |
|---|---|---|
| COSMOS ® 50 FS without polymer | Hypocotyl | 0.1836 |
|  | Rest of plant | 0.0624 |
| COSMOS ® 50 FS with polymer G | Hypocotyl | 1.2882 |
|  | Rest of plant | 0.1537 |

The results show that with the polymer G significant improved root uptake was achieved in seed treatment experiments.

The invention claimed is:

1. A method of combating harmful insects and/or phytopathogenic fungi, which comprises contacting
   (a) plants, seed, soil or habitat of plants in or on which the harmful insects and/or phytopathogenic fungi are growing or may grow, or
   (b) plants, seed or soil to be protected from attack or infestation by said harmful insects or phytopathogenic fungi with an effective amount of a systemicity enhancing pesticide formulation comprising
   at least one pesticide selected from the group consisting of boscalid, fipronil, and mixtures thereof; and
   at least one co-polymer of formula (I)

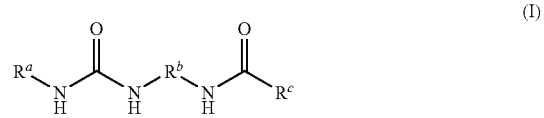

(I)

wherein
$R^a$ is branched or linear $C_6$-$C_{24}$ alkyl, $C_3$-$C_8$ cycloalkyl, $C_3$-$C_8$ cycloalkyl substituted with $C_1$-$C_6$ alkyl, phenyl, phenyl substituted with $C_1$-$C_6$ alkyl, benzyl, benzyl substituted with $C_1$-$C_6$ alkyl, $C_4$-$C_6$ alkyl substituted with $C_4$-$C_{12}$ alkoxy or $C_1$-$C_4$ alkyl substituted with di($C_1$-$C_4$ alkyl)amino;
$R^b$ is derived from diisocyanate and is a (cyclo)aliphatic or aromatic group
$R^c$ is a compound of formula II

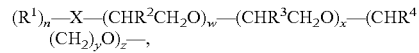

$(R^1)_n$—X—$(CHR^2CH_2O)_w$—$(CHR^3CH_2O)_x$—$(CHR^4(CH_2)_yO)_z$—, wherein
$R^1$ is hydrogen, or branched or linear, saturated or unsaturated $C_{1-40}$-alkyl;
$R^2$, $R^3$, $R^4$ independently of one another are hydrogen or $C_{1-4}$-alkyl;
w, x, z independently of one another correspond to a value of from 0 to 300;
y corresponds to a value of from 1 to 20;
X is N or O,
with the proviso that when n=1, then X=O, or when n=2 then X=N; and the total of w, x and z amounts to at least 1 wherein the formulation comprises from 5 to 60% by weight of the polymer and 3 to 70% by weight of the pesticide(s), whereby the addition of the polymer is performed prior to or after dilution of the formulation in water and wherein the weight ratio of polymer-to-pesticide is 3:7 to 1:3 (w/w) and
wherein the systemicity of the pesticide is enhanced compared to a formulation in which the polymer is absent.

2. A method of controlling undesired vegetation, which comprises allowing a herbicidally effective amount of a systemicity enhancing pesticide formulation comprising
at least one pesticide selected from the group consisting of boscalid, fipronil, and mixtures thereof; and
at least one co-polymer of formula (I)

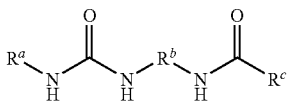
(I)

wherein
$R^a$ is branched or linear $C_6$-$C_{24}$ alkyl, $C_3$-$C_8$ cycloalkyl, $C_3$-$C_8$ cycloalkyl substituted with $C_1$-$C_6$ alkyl, phenyl, phenyl substituted with $C_1$-$C_6$ alkyl, benzyl, benzyl substituted with $C_1$-$C_6$ alkyl, $C_4$-$C_6$ alkyl substituted with $C_4$-$C_{12}$ alkoxy or $C_1$-$C_4$ alkyl substituted with di($C_1$-$C_4$ alkyl)amino;
$R^b$ is derived from diisocyanate and is a (cyclo)aliphatic or aromatic group
$R^c$ is a compound of formula II

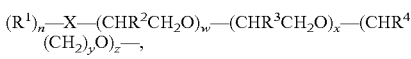

wherein
$R^1$ is hydrogen, or branched or linear, saturated or unsaturated $C_1$-$_{40}$-alkyl;
$R^2$, $R^3$, $R^4$ independently of one another are hydrogen or $C_{1-4}$-alkyl;
w, x, z independently of one another correspond to a value of from 0 to 300;
y corresponds to a value of from 1 to 20;
X is N or O,
with the proviso that when n=1, then X=O, or when n=2 then X=N; and the total of w, x and z amounts to at least 1 wherein the formulation comprises from 5 to 60% by weight of the polymer and 3 to 70% by weight of the pesticide(s), whereby the addition of the polymer is performed prior to or after dilution of the formulation in water and wherein the weight ratio of polymer-to-pesticide is 3:7 to 1:3 (w/w);
to act on plants, their habitat or on seed of said plants wherein the systemicity of the pesticide is enhanced compared to a formulation in which the polymer is absent.

3. A method of improving the health of plants, which comprises applying a systemicity enhancing pesticide formulation comprising
at least one pesticide selected from the group consisting of boscalid, fipronil, and mixtures thereof; and
at least one co-polymer of formula (I)

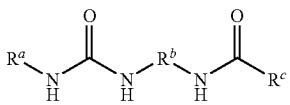
(I)

wherein
$R^a$ is branched or linear $C_6$-$C_{24}$ alkyl, $C_3$-$C_8$ cycloalkyl, $C_3$-$C_8$ cycloalkyl substituted with $C_1$-$C_6$ alkyl, phenyl, phenyl substituted with $C_1$-$C_6$ alkyl, benzyl, benzyl substituted with $C_1$-$C_6$ alkyl, $C_4$-$C_6$ alkyl substituted with $C_4$-$C_{12}$ alkoxy or $C_1$-$C_4$ alkyl substituted with di($C_1$-$C_4$ alkyl)amino;
$R^b$ is derived from diisocyanate and is a (cyclo)aliphatic or aromatic group
$R^c$ is a compound of formula II

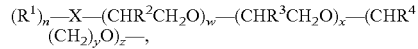

wherein
$R^1$ is hydrogen, or branched or linear, saturated or unsaturated $C_1$-$_{40}$-alkyl;
$R^2$, $R^3$, $R^4$ independently of one another are hydrogen or $C_{1-4}$-alkyl;
w, x, z independently of one another correspond to a value of from 0 to 300;
y corresponds to a value of from 1 to 20;
X is N or O,
with the proviso that when n=1, then X=O, or when n=2 then X=N; and the total of w, x and z amounts to at least 1 wherein the formulation comprises from 5 to 60% by weight of the polymer and 3 to 70% by weight of the pesticide(s), whereby the addition of the polymer is performed prior to or after dilution of the formulation in water and wherein the weight ratio of polymer-to-pesticide is 3:7 to 1:3 (w/w);
to plants, parts of plants, or the locus where plants grow wherein the systemicity of the pesticide is enhanced compared to a formulation in which the polymer is absent.

4. Seeds treated with
a systemicity enhancing pesticide formulation comprising
at least one pesticide selected from the group consisting of boscalid, fipronil, and mixtures thereof; and
at least one co-polymer of formula (I)

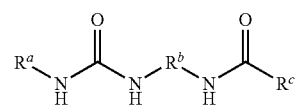
(I)

wherein
$R^a$ is branched or linear $C_6$-$C_{24}$ alkyl, $C_3$-$C_8$ cycloalkyl, $C_3$-$C_8$ cycloalkyl substituted with $C_1$-$C_6$ alkyl, phenyl, phenyl substituted with $C_1$-$C_6$ alkyl, benzyl, benzyl substituted with $C_1$-$C_6$ alkyl, $C_4$-$C_6$ alkyl substituted with $C_4$-$C_{12}$ alkoxy or $C_1$-$C_4$ alkyl substituted with di($C_1$-$C_4$ alkyl)amino;
$R^b$ is derived from diisocyanate and is a (cyclo)aliphatic or aromatic group
$R^c$ is a compound of formula II

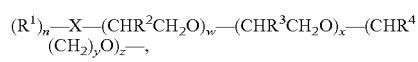

wherein
$R^1$ is hydrogen, or branched or linear, saturated or unsaturated $C_1$-$_{40}$-alkyl;
$R^2$, $R^3$, $R^4$ independently of one another are hydrogen or $C_{1-4}$-alkyl;
w, x, z independently of one another correspond to a value of from 0 to 300;
y corresponds to a value of from 1 to 20;
X is N or O,
with the proviso that when n=1, then X=O, or when n=2 then X=N; and the total of w, x and z amounts to at least 1 wherein the formulation comprises from 5 to 60% by weight of the polymer and 3 to 70% by weight of the pesticide(s), whereby the addition of the polymer is performed prior to or after dilution of the formulation in water and wherein the weight ratio of polymer-to-pesticide is 3:7 to 1:3 (w/w); wherein the systemicity of the pesticide is enhanced compared to a formulation in which the polymer is absent.

5. The method of claim 1, wherein $R^c$ is

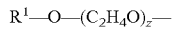

wherein
$R^1$ is hydrogen, or branched or linear, saturated or unsaturated $C_{1-40}$-alkyl;
$R^4$ is hydrogen; and
z corresponds to a value of from 1 to 100.

6. The method of claim 1, wherein z is between 5 and 100.

7. The method of claim 1, wherein $R^b$ is derived from toluene diisocyanate or isophorone diisocyanate.

8. The method of claim 1, wherein $R^a$ is branched or linear $C_6$-$C_{24}$ alkyl, $C_3$-$C_8$ cycloalkyl, phenyl, $C_1$-$C_3$ substituted phenyl, benzyl, $C_4$-$C_6$ alkyl substituted with $C_4$-$C_{12}$ alkoxy or —$C_1$-$C_4$ alkyl substituted with di($C_1$-$C_4$ alkyl)amino.

9. The method of claim 2, wherein $R^c$ is

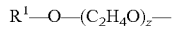

wherein
$R^1$ is hydrogen, or branched or linear, saturated or unsaturated $C_{1-40}$-alkyl;
$R^4$ is hydrogen; and
z corresponds to a value of from 1 to 100.

10. The method of claim 2, wherein z is between 5 and 100.

11. The method of claim 2, wherein $R^b$ is derived from toluene diisocyanate or isophorone diisocyanate.

12. The method of claim 2, wherein $R^a$ is branched or linear $C_6$-$C_{24}$ alkyl, $C_3$-$C_8$ cycloalkyl, phenyl, $C_1$-$C_3$ substituted phenyl, benzyl, $C_4$-$C_6$ alkyl substituted with $C_4$-$C_{12}$ alkoxy or —$C_1$-$C_4$ alkyl substituted with di($C_1$-$C_4$ alkyl)amino.

13. The method of claim 3, wherein $R^c$ is

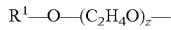

wherein
$R^1$ is hydrogen, or branched or linear, saturated or unsaturated $C_{1-40}$-alkyl;
$R^4$ is hydrogen; and
z corresponds to a value of from 1 to 100.

14. The method of claim 3, wherein z is between 5 and 100.

15. The method of claim 3, wherein $R^b$ is derived from toluene diisocyanate or isophorone diisocyanate.

16. The method of claim 3, wherein $R^a$ is branched or linear $C_6$-$C_{24}$ alkyl, $C_3$-$C_8$ cycloalkyl, phenyl, $C_1$-$C_3$ substituted phenyl, benzyl, $C_4$-$C_6$ alkyl substituted with $C_4$-$C_{12}$ alkoxy or —$C_1$-$C_4$ alkyl substituted with di($C_1$-$C_4$ alkyl)amino.

17. The seeds of claim 4, wherein $R^c$ is

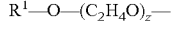

wherein
$R^1$ is hydrogen, or branched or linear, saturated or unsaturated $C_{1-40}$-alkyl;
$R^4$ is hydrogen; and
z corresponds to a value of from 1 to 100.

18. The seeds of claim 4, wherein z is between 5 and 100.

19. The seeds of claim 4, wherein $R^b$ is derived from toluene diisocyanate or isophorone diisocyanate.

20. The seeds of claim 4, wherein $R^a$ is branched or linear $C_6$-$C_{24}$ alkyl, $C_3$-$C_8$ cycloalkyl, phenyl, $C_1$-$C_3$ substituted phenyl, benzyl, $C_4$-$C_6$ alkyl substituted with $C_4$-$C_{12}$ alkoxy or —$C_1$-$C_4$ alkyl substituted with di($C_1$-$C_4$ alkyl)amino.

* * * * *